US005744559A

United States Patent [19]

Nagai et al.

[11] Patent Number: 5,744,559
[45] Date of Patent: Apr. 28, 1998

[54] MACRO-AZO INITIATOR

[75] Inventors: Susumu Nagai, Suita; Hisato Takahashi, Fukuoka; Akira Ueda, Takaishi, all of Japan

[73] Assignee: Wako Pure Chemical Industries, Ltd., Osaka, Japan

[21] Appl. No.: 925,069

[22] Filed: Sep. 8, 1997

Related U.S. Application Data

[63] Continuation of Ser. No. 678,785, Jul. 11, 1996, abandoned, which is a continuation of Ser. No. 434,368, May 3, 1995, abandoned.

[30] Foreign Application Priority Data

Nov. 1, 1994 [JP] Japan .................. 6-292420

[51] Int. Cl.$^6$ ....................................... C08F 4/04
[52] U.S. Cl. .................. 526/219; 526/218.1; 526/255; 526/317.1; 526/319; 526/341; 526/346; 534/588; 534/595
[58] Field of Search ............... 526/219; 534/588, 534/595

[56] References Cited

U.S. PATENT DOCUMENTS 3,763,129  10/1973  Sheppard .
3,863,359  2/1975   Sheppard .
3,956,269  5/1976   Sheppard .................. 526/219
5,010,177  4/1991   Lai ............................ 534/586
5,010,178  4/1991   Lai ............................ 534/586
5,010,179  4/1991   Lai ............................ 526/219
5,037,963  8/1991   Lai ............................ 534/587

FOREIGN PATENT DOCUMENTS 01062318  3/1989  Japan ...................... 526/219
6462318    3/1989  Japan ...................... 526/219
01138207  5/1989  Japan ...................... 526/219

OTHER PUBLICATIONS

Abstract of U.S. Patent No. 3,987,024.
Abstract of U.S. Patent No. 4,075,286.
Abstract of DE-OS 1,940,473.

*Primary Examiner*—Fred Zitomer
*Attorney, Agent, or Firm*—Armstrong, Westerman, Hattori, McLeland & Naughton

[57] ABSTRACT

A macro-azo initiator obtained by reacting a compound (A) having an azo group in the molecule and having a reactive functional group at each end of the molecule with a compound (B) having an azo group in the molecule and having at each end of the molecule a functional group reactive with the reactive functional groups of the compound (A), is effective for a polymerization process of one or more vinyl monomers and a production process of a block polymer.

8 Claims, No Drawings

MACRO-AZO INITIATOR

This application is a continuation of application Ser. No. 08/678,785, filed Jul. 11, 1996, abandoned, which is a continuation of application Ser. No. 08/434,368 filed May 3, 1995, abandoned.

BACKGROUND OF THE INVENTION

The present invention relates to a novel macro-azo initiator having in the molecule two kinds of azo groups which are different in cleavability.

Azo compounds have been widely used as radical initiators for vinyl monomers.

In such circumstances, production of a block polymer using an azo compound has recently been proposed (for example, Ueda and Nagai "Kogaku to Kogyo (Osaka)", 60, 57 (1986)).

Specifically, this production process is as follows: using a linear high-molecular weight azo compound having a plurality of azo groups in the main chain, for example, a compound having repeating units represented by the formula:

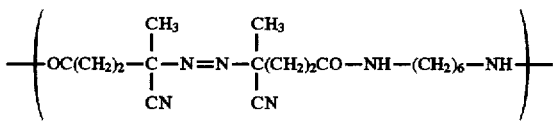

which has been obtained by alternating polycondensation of 4,4'-azobiscyanopentanoyl chloride and a bifunctional compound such as hexamethylenediamine, first-stage polymerization is carried out so as to cleave a certain amount of the azo groups, and second-stage polymerization and succeeding polymerizations are carried out by use of the remaining azo groups. It has been already reported that a block polymer comprising poly(methyl methacrylate) residues and poly(n-butyl acrylate) residues could be efficiently obtained (for example, Ueda and Nagai "Kobunshi Ronbunshu", 44, 469 (1987)).

However, in the above process, the cleavability of the azo groups present in the main chain have the same cleavability (the azo groups are derived from the same azo compound), so that in the first-stage polymerization, the polymerization temperature and the polymerization time should be strictly controlled in order to leave a definite amount of non-cleaved azo groups and use them in the subsequent polymerization.

On the other hand, Shepherd et al. have disclosed the following compounds as compounds having two or more kinds of azo groups which are different in cleavability (for example, the specifications of U.S. Pat. Nos. 3,987,024 and 4,075,286, and DE-OS 1940473):

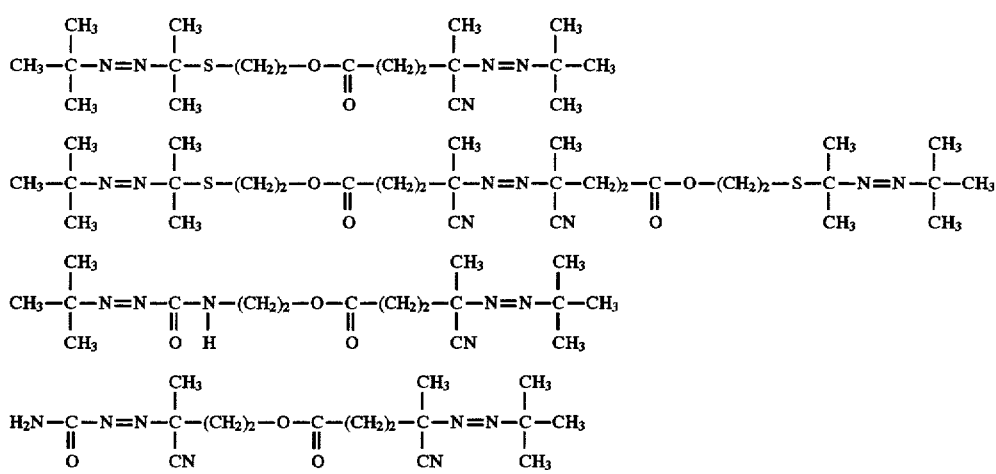

These azo compounds, however, are disadvantageous in that since they have 2 or 3 azo groups in the molecule, polymerization using any of them as an polymerization initiator causes formation of a large number of radicals from the ends of the initiator which do not participate in block formation.

SUMMARY OF THE INVENTION

The present invention was made in view of such conditions and is intended to provide a novel macro-azo initiator which does not require the strict control and permits easy and efficient production of a block polymer.

The present invention provides a macro-azo initiator obtained by reacting a compound (A) having an azo group in the molecule and having a reactive functional group at each end of the molecule with a compound (B) having an azo group in the molecule and having at each end of the molecule a functional group reactive with the reactive functional groups of the compound (A).

The present invention also provides a process for polymerizing at least one vinyl monomer characterized by using the aforesaid macro-azo initiator.

In addition, the present invention provides a process for producing a block polymer characterized by using the aforesaid macro-azo initiator.

Further, the present invention provides a macro-azo initiator comprising repeating units represented by the formula:

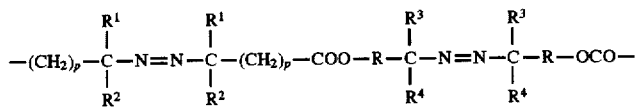

wherein $R^1$, $R^2$, $R^3$ and $R^4$ are independently a hydrogen atom, a lower alkyl group preferably having 1 to 6 carbon atoms or a cyano group; R is —(CH$_2$)q—, —COO(CH$_2$)$_q$— or —CONH(CH$_2$)$_q$—; q is an integer of 1 to 6; and p is an integer of 1 to 6.

DESCRIPTION OF THE PREFERRED EMBODIMENTS

As the compound (A) having an azo group in the molecule and having a reactive functional group at each end of the molecule which is used in the present invention, any compound may be used so long as it has an azo group in the molecule and has at each end of the molecule a reactive functional group such as —COOH group, —COCl group, —COBr group, —COOCH$_3$ group, —COOC$_2$H$_5$ group, —NCO group or the like. Typical examples of the compound (A) are the following compounds:

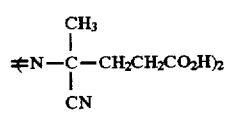 (A-1)

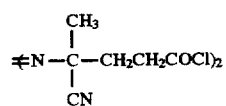 (A-2)

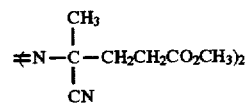 (A-3)

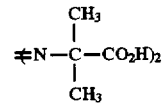 (A-4)

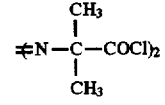 (A-5)

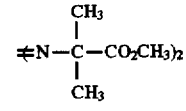 (A-6)

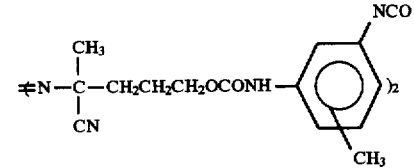 (A-7)

As the compound (B) having an azo group in the molecule and having at each end of the molecule a functional group reactive with the reactive functional groups of the compound (A) which is used in the present invention, any compound may be used so long as it has an azo group in the molecule and has at each end of the molecule a functional group reactive with the reactive functional groups of the compound (A) (e.g. any of above-exemplified reactive functional groups), such as —OH group, —NH$_2$ group, —NH— group or the like. Typical examples of the compound (B) are the following compounds:

 (B-1)

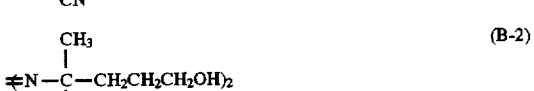 (B-2)

 (B-3)

 (B-4)

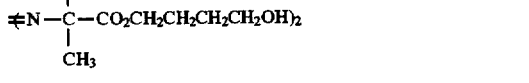 (B-5)

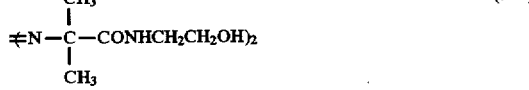 (B-6)

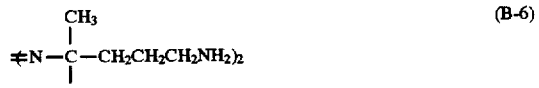 (B-7)

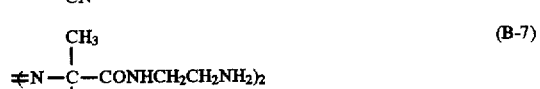 (B-8)

 (B-9)

 (B-10)

The macro-azo initiator of the present invention obtained by reacting the compound (A) according to the present invention with the compound (B) according to the present invention are represented by the formula [I]', and specific examples of the macro-azo initiator are compounds comprising any of the repeating units described below. Needless to say, the macro-azo initiator is not limited to these compounds.

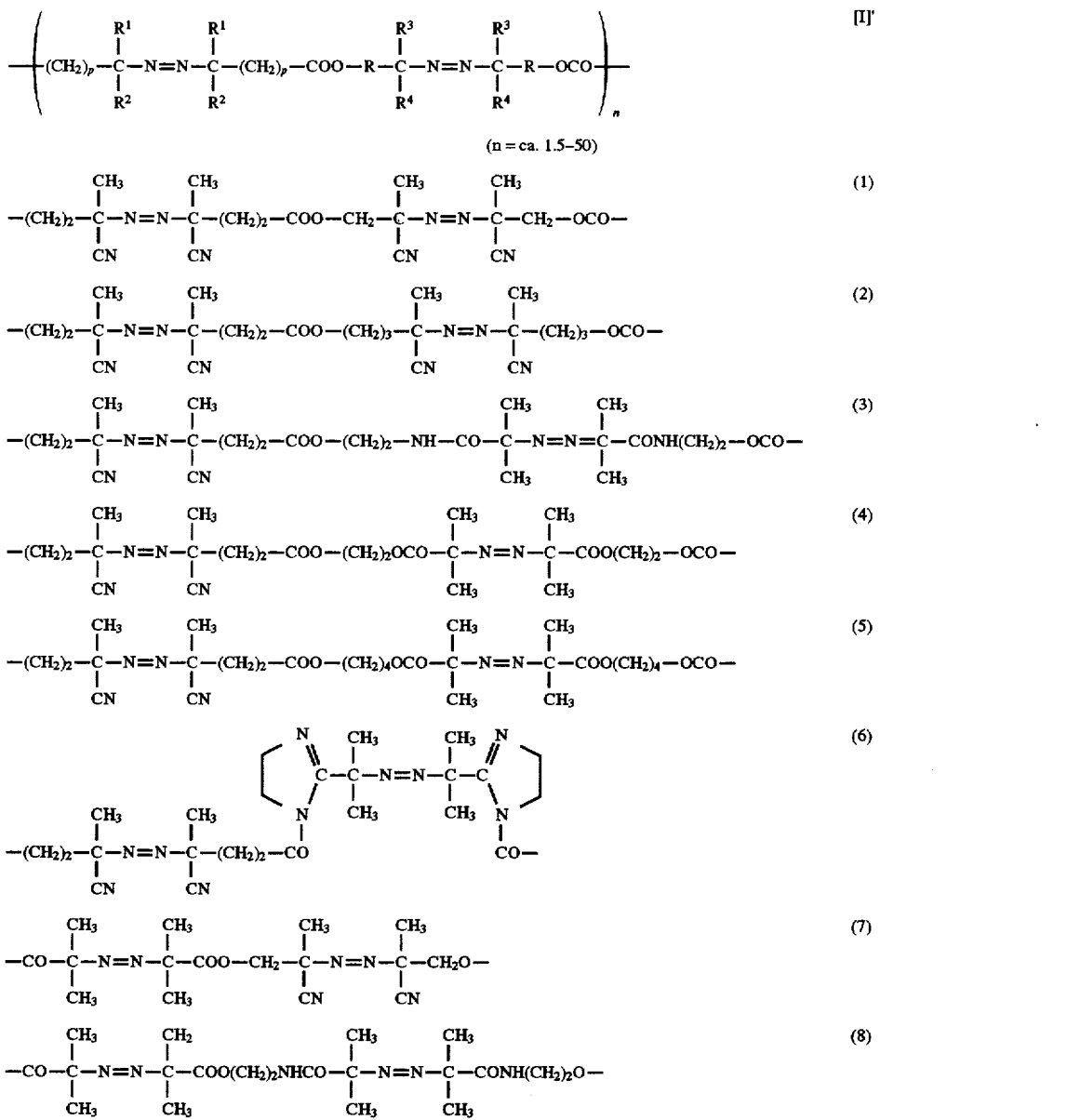

In the macro-azo initiator comprising repeating units of the formula [I] of the present invention, as the lower alkyl groups represented by $R^1$ through $R^4$, respectively, there can be exemplified methyl group, ethyl group, propyl group, butyl group, amyl group, etc., which may be either linear or branched. Specific examples of the macro-azo initiator comprising repeating units of the formula [I] of the present invention are compounds comprising any of the repeating units of the above formulas (1) to (5). Needless to say, the macro-azo initiator is not limited to these compounds.

Processes for producing the macro-azo initiator of the present invention are described below by taking the case where a dibasic acid represented by the formula:

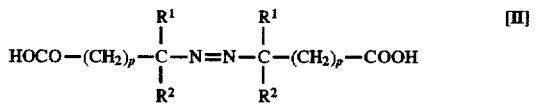

(wherein $R^1$, $R^2$ and p are as defined above) is used as the compound (A) and a diol represented by the formula:

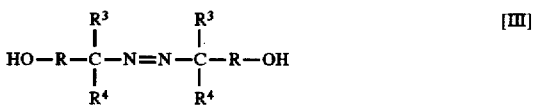

(wherein R, $R^3$ and $R^4$ are as defined above) is used as the compound (B).

As a process for producing the compound of the present invention by using the dibasic acid of the formula [II] and the diol of the formula [III] as starting materials, there are a process of converting the dibasic acid of the formula [II] into a dibacic acid dihalide and then reacting the dihalide with the diol of the formula [III], and a process of directly reacting the dibasic acid of the formula [II] with the diol of the formula [III] by use of a dehydrating-condensation agent.

When the compound of the present invention is produced by converting the dibasic acid of the formula [II] into a dibacic acid dihalide and then reacting the dihalide with the diol of the formula [III], it is usually preferable to carry out the reaction in the presence of a base catalyst. The base catalyst includes, for example, triethylamine, tributylamine, trihexylamine, pyridine, picoline, 4-pyrrolidino-pyridine, 4-dimethylaminopyridine, dimethylaniline and piperidine.

The dehydrating-condensation agent used for producing the compound of the present invention by the direct reaction includes, for example, dicyclohexyl-carbodiimide, diisopropylcarbodiimide and 1-ethyl-3-(3-dimethylaminopropyl) carbodiimide hydrochloride. A catalyst used for the direct reaction includes the above-exemplified base catalysts, but employment of a basic catalyst is not always necessary.

Both of the reactions in the above production processes, respectively, are carried out usually in a solvent. The solvent includes, for example, ethers such as tetrahydrofuran, diethyl ether, dioxane, etc.; halogenated hydrocarbons such as chloroform, methylene chloride, 1,2-dichloroethane, etc.; hydrocarbons such as n-hexane, petroleum ether, toluene, benzene, xylene, etc.; ketones such as acetone, methyl ethyl ketone, methyl isobutyl ketone, etc.; acetonitrile; N,N-dimethylformamide; and dimethyl sulfoxide. These solvents may be used singly or in proper combination of two or more thereof. All of them are preferably dried solvents.

The proportions of the dibasic acid of the formula [II] (or the dibasic acid dihalide obtained therefrom) and the diol of the formula [III] are not critical, though usually, these compounds are preferably used in substantially equimolar amounts in order to obtain the compound of the present invention having a higher molecular weight.

When the basic catalyst is used, its amount is usually preferably 0 (no catalyst) to about 120 mole % based on the number of moles of the starting compound [III].

Although the amount of the solvent used is properly varied depending on the viscosity of the reaction solution, etc., it is preferably about 100 to about 5,000 wt. % based on the weight of the starting compound [III].

Although not critical, the reaction temperature is suitably about −20° C. to about 50° C. in both of the above processes. For preventing the cleavage of the azo groups and obtaining a product having a high molecular weight, the reaction temperature is more preferably about 15° C. to about 35° C. The reaction temperature may be raised stepwise from a low temperature to a high temperature.

Although not critical, the reaction time is usually about 0.1 to about 48 hours, preferably 0.5 to 8 hours.

The compound of the present invention thus obtained is an oligomer having a degree of polymerization n of about 1.5 to about 50, usually about 1.5 to about 20. Although said compound varies in properties, depending on the starting compounds and the molecular weight, it is usually a colorless or light-yellow, powdery or viscous substance. Although said compound varies also in solubility similarly, it is usually soluble in acetone, methyl ethyl ketone, tetrahydrofuran, chloroform, etc.

In the compound of the present invention, the azo groups are easily cleaved by heating or light irradiation to generate nitrogen gas and cause production of radical species. In this case, when any of various vinyl monomers is present, it is rapidly polymerized.

The compound of the present invention is characterized by having in the molecule two kinds of azo groups which are different in cleavability.

By virtue of this characteristic, a block polymer can easily be obtained by choosing conditions under which azo groups having a high cleavability are preferentially cleaved at first with substantially no cleavage of azo groups having a low cleavability, thereby obtaining a polymer retaining the azo groups having a low cleavability, and then carrying out the second-stage polymerization and succeeding polymerizations by utilizing the remaining azo groups having a low cleavability.

As vinyl monomers used in the production of a block polymer using the compound of the present invention, any vinyl monomers may be used so long as they are polymerized by radical reaction. There can be exemplified styrene, methacrylic acid or an ester thereof, acrylic acid or an ester thereof, vinyl chloride, acrylonitrile, vinyl acetate, vinylidene chloride, tetrafluoroethylene, etc. The vinyl monomers are not limited thereto. The above-exemplified vinyl monomers may be used singly or in proper combination of two or more thereof.

The production of a block polymer using the compound of the present invention can be carried out by any of polymerization methods such as solution polymerization, bulk polymerization, suspension polymerization, emulsion polymerization, etc.

A solvent used in the solution polymerization includes, for example, ethers such as tetrahydrofuran, diethyl ether, dioxane, etc.; halogenated hydrocarbons such as chloroform, methylene chloride, 1,2-dichloroethane, etc.; hydrocarbons such as n-hexane, petroleum ether, toluene, benzene, xylene, etc.; alcohols such as methanol, ethanol, isopropanol, etc.; ketones such as acetone, methyl ethyl ketone, methyl isobutyl ketone, etc.; acetonitrile; N,N-dimethylformamide; and dimethyl sulfoxide. These solvents may be used singly or in proper combination of two or more thereof.

The proportions of the compound of the present invention and the vinyl monomer used in the above production of a block polymer are varied depending on the kind of the compound of the present invention used. In general, they can be chosen in wide ranges. Usually, the proportion of the vinyl monomer is preferably in the range of 0.5 to 1,000 parts by weight per part by weight of the compound of the present invention.

When a solvent or a dispersant is used, the amount of the solvent or dispersant is usually about 1 to about 2,000 parts by weight per part by weight of the compound of the present invention.

Although the reaction temperature is varied a little in view of other polymerization conditions, it is usually chosen in the range of 30°–130° C. For obtaining a block polymer efficiently, it is preferable to carry out the first-stage polymerization at a low temperature and the second-stage polymerization and succeeding polymerizations at a high temperature.

Although the reaction time is varied depending on purposes and in view of other polymerization conditions, a suitable reaction time in each polymerization stage is usually about 1 to about 48 hours.

Thus, employment of the compound of the present invention permits easy and very efficient production of a block polymer.

As described above, the compound of the present invention can be suitably used for producing a block polymer. Moreover, needless to say, it can be effectively used also as an ordinary radical initiator.

The present invention is illustrated below in further detail with reference to Examples, which are not by way of limitation but by way of illustration.

The abbreviations used in the Examples, Referential Examples and Comparative Examples described below stand for the following real names:

ACPC: 4,4'-azobis(4-cyanopentanoyl chloride)
ACPA: 4,4'-azobis(4-cyanopentanoic acid)
ACPO: 2,2'-azobis(2-cyanopropanol)

AHPA: 2,2'-azobis[(2-methyl-N-(2-hydroxy-ethyl)propionamide]
MMA : methyl methacrylate
PMMA: poly(methyl methacrylate)

EXAMPLE 1
Polycondensation of ACPO and ACPC

After 1.00 g (5 mmoles) of ACPO, 1.29 g (12.7 mmoles) of triethylamine and 5 ml of chloroform were mixed, a solution of 1.58 g (5 mmoles) of ACPC in 5 ml of chloroform was added dropwise with stirring and ice-cooling over a period of about 10 minutes. After completion of the dropwise addition, 5 ml of chloroform was added and the resulting mixture was stirred at room temperature for 24 hours, followed by filtering off the insoluble material. The filtrate was washed three times with water, dried over anhydrous sodium sulfate, and then the drying agent was filtered. The resulting filtrate was concentrated to dryness to obtain 1.27 g of a polycondensate (hereinafter abbreviated as MAI [1]). Yield: 57.1%.

The molecular weight distribution of the polycondensate was measured by gel-permeation chromatography (GPC) to find that the molecular weight was distributed in the range of 550 to 2080 (degree of polymerization n=1.5 to 4.5). The pyrolytic behavior of the polycondensate was followed by means of a differential scanning calorimeter (DSC) to find that the polycondensate had decomposition peaks at 122.9° C. and 132° C. In addition, IR measurement confirmed the appearance of a peak near 1750 $cm^{-1}$ due to an ester linkage.

EXAMPLE 2
Polycondensation of ACPO and ACPC

The reaction of ACPO with ACPC was carried out in exactly the same manner as described in Example 1 except for using tetrahydrofuran as a solvent in place of chloroform. After completion of the reaction, the reaction mixture was filtered and the filtrate was concentrated to dryness, followed by extraction from the residue with chloroform. The extract solution was washed with water, dried and then filtered, and the resulting filtrate was concentrated to dryness to obtain 1.29 g of a polycondensate. Yield: 58.1%.

As a result of measurement by GPC, it was found that the polycondensate obtained had a molecular weight distribution in the range of 550 to 2740 (degree of polymerization n=1.5 to 6.5). The results of measurement with DSC and IR measurement were the same as those obtained in Example 1.

EXAMPLE 3
Polycondensation of AHPA and ACPC

After 2.88 g (10 mmoles) of AHPA, 2.50 g (24.7 mmoles) of triethylamine and 20 ml of chloroform were mixed, a solution of 3.17 g (10 mmoles) of ACPC in 20 ml of chloroform was added dropwise with stirring and ice-cooling over a period of about 20 minutes. After completion of the dropwise addition, 20 ml of chloroform was added and the resulting mixture was stirred at room temperature for 24 hours, followed by filtering off the insoluble material. The filtrate was washed three times with water, dried over anhydrous sodium sulfate, and then the drying agent was filtered. The resulting filtrate was concentrated to dryness to obtain 3.47 g of a polycondensate (hereinafter abbreviated as MAI [2]). Yield: 65.1%.

The molecular weight distribution of the polycondensate was measured by GPC to find that the molecular weight was distributed in the range of 670 to 1580 (degree of polymerization n=1.5 to 3.5). As a result of measurement with DSC, the polycondensate was found to have decomposition peaks at 120.5° C. and 159.4° C. In addition, IR measurement confirmed the appearance of a peak near 1750 $cm^{-1}$ due to an ester linkage.

Referential Example 1
Polycondensation of bisphenol-Z and ACPC

After 2.64 g (10 mmoles) of bisphenol-Z, 2.50 g (24.7 mmoles) of triethylamine and 10 ml of chloroform were mixed, a solution of 3.17 g (10 mmoles) of ACPC in 10 ml of chloroform was added dropwise with stirring and ice-cooling over a period of about 20 minutes. After completion of the dropwise addition, 10 ml of chloroform was added and the resulting mixture was stirred at room temperature for 24 hours. Then, the reaction mixture was washed three times with water and dried over anhydrous sodium sulfate. The drying agent was filtered off and the filtrate was concentrated to dryness to obtain 4.76 g of a polycondensate (hereinafter abbreviated as MAI [3]). Yield: 93.8%.

Result of measurement by GPC: the polycondensate had a molecular weight distribution in the range of 760 to 6700 (degree of polymerization n=1.5 to 13.0).

Result of measurement with DSC: a decomposition peak appeared at 116.8° C.

IR: a peak near 1750 $cm^{-1}$ due to an ester linkage appeared.

EXAMPLE 4
Polymerization of styrene using MAI [1]

To 4.68 g of styrene monomer was added a solution in N,N-dimethylformamide (5 ml) of 0.16 g of the MAI [1] obtained in Example 1, and the reaction was carried out with shaking in a sealed tube at 70° C. for 8 hours. After completion of the reaction, the reaction mixture was poured into a large volume of methanol to form a precipitate, and the precipitate was collected by filtration and dried to obtain 2.85 g of a polystyrene containing azo groups. Yield: 58.8%.

The molecular weight (Mp) of the polystyrene indicated by a maximum peak in GPC was 76,400.

EXAMPLE 5
Polymerization of MMA using MAI [1]

Reaction and after-treatment were carried in exactly the same manner as described in Example 4 except for using 1.50 g of MMA in place of 4.68 g of styrene, to obtain 1.40 g of PMMA containing azo groups. Yield: 84.2%.

Mp=30,100.

EXAMPLES 6 to 8

Reaction and after-treatment were carried in exactly the same manner as described in Example 4 except for changing the reaction temperature to 80° C. and the reaction time to 2, 4 or 6 hours. Thus, polystyrenes containing azo groups were obtained. The results obtained are shown in Table 1.

TABLE 1

| Example | Reaction temp. (°C.) | Reaction time (hr.) | Amount (g) | Yield (%) | Mp |
|---|---|---|---|---|---|
| 6 | 80 | 2 | 2.04 | 42.1 | 52,200 |
| 7 | 80 | 4 | 2.81 | 58.1 | 57,500 |
| 8 | 80 | 6 | 3.21 | 66.3 | 57,500 |

EXAMPLE 9

Production of a styrene-MMA block polymer using MAI [1]

(1) First-stage polymerization of styrene using MAI [1]

To 4.68 g of styrene monomer was added a solution in N,N-dimethylformamide (5 ml) of 0.138 g of the MAI [1] obtained in Example 1 (molar quantity of azo group of the ACPA portion: 0.314 mmole, molar quantity of azo group of the ACPO portion: 0.314 mmole, total molar quantity of the azo groups: 0.628 mmole), and the reaction was carried out with shaking in a sealed tube at each predetermined temperature for each predetermined time. After completion of the reaction, the reaction mixture was poured into a large volume of methanol to form a precipitate, and the precipitate was collected by filtration and dried to obtain a polystyrene containing azo groups (the polystyrene is hereinafter abbreviated as PSt*-[1]). The results obtained are shown in Table 2.

(2) Second-stage polymerization of MMA using PSt*-[1]

To 1.00 g of MMA monomer was added a solution in N,N-dimethylformamide (10 ml) of 0.50 g of the PSt*-[1] obtained in (1) above, and the reaction was carried out with shaking in a sealed tube at each predetermined temperature for 24 hours. After completion of the reaction, the reaction mixture was poured into a large volume of methanol to form a precipitate, and the precipitate was collected by filtration and dried to obtain a styrene-MMA block polymer. The results obtained are shown in Table 3.

EXAMPLE 10

Production of a styrene-MMA block polymer using MAI [2]

(1) First-stage polymerization of styrene using MAI [2]

Reaction and after-treatment were carried out in exactly the same manner as described in Example 9 (1), except that in place of the MAI [1], the MAI [2] obtained in Example 3 was used in such an amount that the molar quantities of the azo groups were the same as in the case of the MAI [1] (ACPA portion: 0.314 mmole, AHPA portion: 0.314 mmole, total: 0.628 mmole), whereby a polystyrene containing azo groups (the polystyrene is hereinafter abbreviated as PSt*-[2]) was obtained. The results obtained are shown in Table 2.

(2) Second-stage polymerization of MMA using PSt*-[2]

Reaction and after-treatment were carried out in exactly the same manner as described in Example 9 (2) except for using PSt*-[2] in place of PSt*-[1], to otain a styrene-MMA block polymer. The results obtained are shown in Table 3.

Comparative Example 1

Production of a styrene-MMA block polymer using MAI [3]

(1) First-stage polymerization of styrene using MAI [3]

Reaction and after-treatment were carried out in exactly the same manner as described in Example 9 (1), except that in place of the MAI [1], the MAI [3] obtained in Referential Example 1 was used in such an amount that the molar quantity of azo group was the same as in the case of MAI [1] (ACPA portion: 0.628 mmole), whereby a polystyrene containing azo groups (the polystyrene is hereinafter abbreviated as PSt*-[3]) was obtained. The results obtained are shown in Table 2.

(2) Second-stage polymerization of MMA using PSt *-[3]

Reaction and after-treatment were carried out in exactly the same manner as described in Example 9 (2) except for using PSt*-[3] in place of PSt*-[1], to obtain a styrene-MMA block polymer. The results obtained are shown in Table 3.

TABLE 2

| Example | Initiator (g) | Reaction temp. (°C.) | Reaction time (hr.) | Polystyrene containing azo groups Amount (g) | Yield (%) |
|---|---|---|---|---|---|
| Example 9 (1) | MAI [1] 0.138 | 60 | 24 | 2.96 | 61.4 |
| | | 70 | 12 | 2.60 | 54.0 |
| | | 80 | 12 | 3.18 | 66.1 |
| Example 10 (1) | MAI [2] 0.168 | 60 | 24 | 2.88 | 59.5 |
| | | 70 | 12 | 2.78 | 57.3 |
| | | 80 | 12 | 3.13 | 64.5 |
| Comparative Example 1 (1) | MAI [3] 0.320 | 60 | 24 | 3.46 | 69.1 |
| | | 70 | 12 | 3.15 | 63.0 |
| | | 80 | 12 | 3.46 | 69.3 |

As is clear from Table 2, in the first-stage polymerization, the azo group of the ACPA portion which has the highest cleavability is dominant, so that the polymerization conversion is greatly dependent on the quantity of said azo group. On the other hand, it is conjectured that the azo group of the ACPO portion and the azo group of the AEPA portion have a lower cleavability than does the azo group of the ACPA portion, and hence are reserved almost no cleavage in the first-stage polymerization.

TABLE 3

| Example | Polystyrene containing azo groups | Conditions of the first-stage polymerization Temp. (°C.) | Time (hr.) | Styrene-MMA block polymer Reaction temp. 70° C. Amount (g) | Yield (%) | Reaction temp. 80° C. Amount (g) | Yield (%) |
|---|---|---|---|---|---|---|---|
| Example 9 (2) | PSt*-[1] | 60 | 24 | 1.20 | 69.6 | 1.33 | 82.7 |
| | | 70 | 12 | 1.19 | 69.5 | 1.27 | 76.7 |
| | | 80 | 12 | 0.99 | 48.6 | 1.08 | 58.2 |
| Example 10 (2) | PSt*-[2] | 60 | 24 | 1.26 | 76.3 | 1.38 | 87.9 |
| | | 70 | 12 | 1.04 | 53.6 | 1.28 | 78.4 |
| | | 80 | 12 | 1.07 | 56.9 | 1.06 | 56.4 |
| Comparative Example 1 (2) | PSt*-[3] | 60 | 24 | 1.16 | 66.1 | 1.17 | 66.6 |
| | | 70 | 12 | 0.86 | 45.6 | 0.89 | 48.8 |
| | | 80 | 12 | 0.66 | 16.4 | 0.82 | 42.6 |

As is clear from Table 3, the polymerization of MMA using any of PSt*-[1] and PSt*-[2] according to the present invention was clearly superior in polymerization conversion to the polymerization of MMA using PSt*-[3], i.e. a known polystyrene containing azo groups, and gave a styrene-MMA block polymer in high yield. The reason is presumed as follow: the azo group of the ACPO portion or the AEPA portion reserved in the first-stage polymerization acted effectively in the second-stage polymerization.

As described above, the present invention provides a novel macro-azo initiator having in the molecule two kinds of azo groups which are different in cleavability, and the present invention is markedly effective in that a block polymer can be effectively produced by carrying out multistage polymerization using the macro-azo initiator of the present invention.

What is claimed is:

1. A macro-azo initiator comprising a mixture of oligomers obtained in one reaction, each oligomer having at least two kinds of azo groups different in cleavability and obtained by reacting a compound (A) having an azo group in the molecule and having a reactive functional group selected from the group consisting of a —COOH group, a —COCl group, a —COBr group, a —COOCH$_3$ group, a —COOC$_2$H$_5$ group and an —NCO group at each end of the molecule with a compound (B) having an azo group in the molecule and having at each end of the molecule a functional group selected from the group consisting of an —OH group, an —NH$_2$ group and an —NH— group, reactive with the reactive functional group of compound (A).

2. In a process for polymerizing at least one vinyl monomer, the improvement which comprises the process of using the macro-azo initiator of claim 1.

3. In a process for producing a block polymer, the improvement which comprises the process of using the macro-azo initiator of claim 1.

4. A macro-azo initiator comprising a mixture, of oligomers obtained in one reaction, each oligomer having at least repeating units represented by the formula:

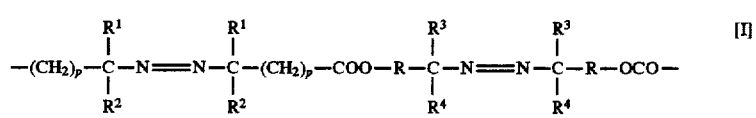

wherein R$^1$, R$^2$, R$^3$ and R$^4$ are independently a hydrogen atom, a lower alkyl group or a cyano group; R is —(CH$_2$)$_q$—, —COO(CH$_2$)$_q$— or —CONH(CH$_2$)$_q$; q is an integer of 1 to 6; and p is an integer of 1 to 6, wherein the oligomer mixture has a degree of polymerization of about 1.5 to 50.

5. A macro-azo initiator according to claim 4, wherein the repeating unit is represented by the formula:

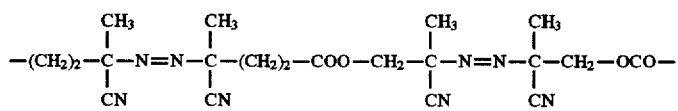

and the oligomer mixture has a degree of polymerization of about 1.5 to 50.

6. A macro-azo initiator according to claim 1, wherein the compound (A) is

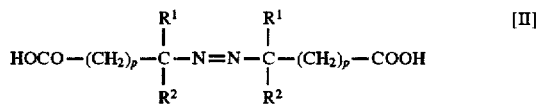

wherein R$^1$ and R$^2$ are independently a hydrogen atom, a lower alkyl group or a cyano group; and p is an integer of 1 to 6, and the compound (B) is

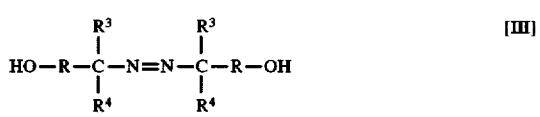

wherein R$^3$ and R$^4$ are independently a hydrogen atom, a lower alkyl group or a cyano group; R is —(CH$_2$)$_6$—, —COO(CH$_2$)$_q$— or —CONH(CH$_2$)$_q$—; and q is an integer of 1 to 6.

7. A process for polymerizing at least one vinyl monomer according to claim 2, wherein the vinyl monomer is selected from the group consisting of styrene, methacrylic acid or an ester thereof, acrylic acid or an ester thereof, vinyl chloride, acrylonitrile, vinyl acetate, vinylidene chloride, and tetrafluoroethylene.

8. The macro-azo initiator of claim 1 wherein said compound (A) is selected from the group consisting of the following formulae (A-1) through (A-7):

-continued (A-2)
$$\equiv N-\underset{CN}{\overset{CH_3}{\underset{|}{C}}}-CH_2CH_2COCl)_2$$

(A-3)
$$\equiv N-\underset{CN}{\overset{CH_3}{\underset{|}{C}}}-CH_2CH_2CO_2CH_3)_2$$

(A-4)
$$\equiv N-\underset{CH_3}{\overset{CH_3}{\underset{|}{C}}}-CO_2H)_2$$

(A-5)
$$\equiv N-\underset{CH_3}{\overset{CH_3}{\underset{|}{C}}}-COCl)_2$$

(A-6)
$$\equiv N-\underset{CH_3}{\overset{CH_3}{\underset{|}{C}}}-CO_2CH_3)_2$$

(A-7)
$$\equiv N-\underset{CN}{\overset{CH_3}{\underset{|}{C}}}-CH_2CH_2CH_2OCONH-\underset{CH_3}{\underset{}{\bigcirc}}-NCO)_2$$

and said compound (B) is selected from the group consisting of the following formulae (B-1) to (B-10):

(B-1)
$$\equiv N-\underset{CN}{\overset{CH_3}{\underset{|}{C}}}-CH_2OH)_2$$

(B-2)
$$\equiv N-\underset{CN}{\overset{CH_3}{\underset{|}{C}}}-CH_2CH_2CH_2OH)_2$$

(B-3)
$$\equiv N-\underset{CH_3}{\overset{CH_3}{\underset{|}{C}}}-CO_2CH_2CH_2OH)_2$$

(B-4)
$$\equiv N-\underset{CH_3}{\overset{CH_3}{\underset{|}{C}}}-CO_2CH_2CH_2CH_2CH_2OH)_2$$

(B-5)
$$\equiv N-\underset{CH_3}{\overset{CH_3}{\underset{|}{C}}}-CONHCH_2CH_2OH)_2$$

(B-6)
$$\equiv N-\underset{CN}{\overset{CH_3}{\underset{|}{C}}}-CH_2CH_2CH_2NH_2)_2$$

(B-7)
$$\equiv N-\underset{CH_3}{\overset{CH_3}{\underset{|}{C}}}-CONHCH_2CH_2NH_2)_2$$

(B-8)
$$\equiv N-CONH_2)_2$$

(B-9)
$$\equiv N-\underset{CH_3}{\overset{CH_3}{\underset{|}{C}}}-\underset{NH_2}{\overset{NH}{\underset{}{C}}})_2$$

(B-10)
$$\equiv N-\underset{CH_3}{\overset{CH_3}{\underset{|}{C}}}-\overset{N}{\underset{\underset{H}{N}}{C}})_2$$

* * * * *